(12) United States Patent
Weber et al.

(10) Patent No.: US 8,348,991 B2
(45) Date of Patent: Jan. 8, 2013

(54) STENT WITH OVERLAP AND HIGH EXPANSION

(75) Inventors: Jan Weber, Maastricht (NL); Karl A. Jagger, Deephaven, MN (US); Tracee Eidenschink, Wayzata, MN (US); James Anderson, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 579 days.

(21) Appl. No.: 11/755,592

(22) Filed: May 30, 2007

(65) Prior Publication Data

US 2007/0233270 A1 Oct. 4, 2007

Related U.S. Application Data

(63) Continuation-in-part of application No. 11/392,047, filed on Mar. 29, 2006, now Pat. No. 8,043,358.

(51) Int. Cl.
A61F 2/06 (2006.01)

(52) U.S. Cl. .................................................... 623/1.15

(58) Field of Classification Search ................ 623/1.15, 623/1.16, 1.3, 1.31, 1.35, 1.14, 1.32, 1.42, 623/1.43, 1.36; 606/108, 192, 195
See application file for complete search history.

(56) References Cited

U.S. PATENT DOCUMENTS

| 4,485,387 A | 11/1984 | Drumheller | 346/14 |
| 4,994,071 A | 2/1991 | Gregor | 606/194 |
| 5,091,205 A | 2/1992 | Fan | 427/2 |
| 5,630,829 A | 5/1997 | Lauterjung | 606/198 |
| 5,755,770 A | 5/1998 | Ravenscroft | 623/1 |
| 5,755,774 A | 5/1998 | Pinchuk | |
| 5,755,776 A | 5/1998 | Al-Saadon | 623/1 |
| 5,776,161 A | 7/1998 | Globerman | 606/194 |
| 5,800,526 A | 9/1998 | Anderson et al. | 623/1.16 |
| 5,824,046 A | 10/1998 | Smith et al. | 623/1 |
| 5,836,966 A * | 11/1998 | St. Germain | 606/198 |
| 5,843,120 A | 12/1998 | Israel et al. | 606/198 |
| 5,876,449 A | 3/1999 | Starck et al. | 623/12 |
| 5,906,640 A | 5/1999 | Penn et al. | 623/1 |
| 5,922,021 A | 7/1999 | Jang | 623/1 |
| 5,957,930 A | 9/1999 | Vrba | 606/108 |
| 5,989,639 A | 11/1999 | Person | 427/356 |
| 6,006,665 A | 12/1999 | Stuchlik et al. | 101/325.13 |

(Continued)

FOREIGN PATENT DOCUMENTS

EP 1159934 12/2001

(Continued)

OTHER PUBLICATIONS

U.S. Appl. No. 11/392,047, filed Mar. 29, 2006, Weber et al.

*Primary Examiner* — Kathleen Sonnett
*Assistant Examiner* — Jocelin Tanner
(74) *Attorney, Agent, or Firm* — Vidas, Arrett & Steinkraus

(57) ABSTRACT

A stent can comprise a tubular body having a first region and a second region. The tubular body is defined by a plurality of serpentine bands. Each serpentine band comprises a plurality of alternating proximal turns and distal turns connected by struts. The second region comprises a first serpentine band and a second serpentine band that overlap one another about a common stent circumference. The first region comprises a serpentine band that is not overlapped by another serpentine band about a common stent circumference.

20 Claims, 14 Drawing Sheets

U.S. PATENT DOCUMENTS

| | | | | |
|---|---|---|---|---|
| 6,013,091 | A | 1/2000 | Ley et al. | 83/15 |
| 6,017,363 | A | 1/2000 | Hojeibane | 623/1 |
| 6,030,414 | A | 2/2000 | Taheri | 623/1 |
| 6,033,433 | A | 3/2000 | Ehr | 623/1 |
| 6,048,361 | A | 4/2000 | Van Gepen | 623/1 |
| 6,056,775 | A | 5/2000 | Borghi | 623/1.16 |
| 6,113,627 | A | 9/2000 | Jang | 623/1 |
| 6,120,522 | A | 9/2000 | Vrba et al. | 606/19 |
| 6,123,712 | A | 9/2000 | DiCaprio et al. | 606/108 |
| 6,123,721 | A | 9/2000 | Jang | 623/1 |
| 6,129,754 | A | 10/2000 | Kanesaka | 623/1 |
| 6,168,621 | B1 | 1/2001 | Vrba | 623/1.2 |
| 6,193,747 | B1 | 2/2001 | von Oepen | 623/1.15 |
| 6,200,334 | B1 | 3/2001 | Jang | 623/1.1 |
| 6,210,429 | B1 | 4/2001 | Vardi | 623/1.11 |
| 6,231,598 | B1 * | 5/2001 | Berry et al. | 623/1.15 |
| 6,251,134 | B1 | 6/2001 | Alt et al. | 623/1.16 |
| 6,258,116 | B1 | 7/2001 | Hojeibane | 623/1.16 |
| 6,270,524 | B1 | 8/2001 | Kim | 623/1.15 |
| 6,290,673 | B1 | 9/2001 | Shanley | 604/102.02 |
| 6,312,367 | B1 | 11/2001 | Rogge | 492/35 |
| 6,325,826 | B1 * | 12/2001 | Vardi et al. | 623/1.35 |
| 6,331,189 | B1 | 12/2001 | Wolinsky et al. | 623/1.15 |
| 6,334,870 | B1 | 1/2002 | Ehr | 623/1.16 |
| 6,348,065 | B1 | 2/2002 | Brown et al. | 623/1.16 |
| 6,361,555 | B1 | 3/2002 | Wilson | 623/1.11 |
| 6,409,753 | B1 | 6/2002 | Brown et al. | 623/1.16 |
| 6,432,132 | B1 | 8/2002 | Cottone et al. | 623/1.15 |
| 6,436,134 | B2 | 8/2002 | Richter | 623/1.15 |
| 6,464,722 | B2 | 10/2002 | Israel et al. | 623/1.17 |
| 6,468,302 | B2 | 10/2002 | Cox et al. | 623/1.15 |
| 6,506,211 | B1 | 1/2003 | Skubitz et al. | |
| 6,511,491 | B2 | 1/2003 | Grudem et al. | 623/1.11 |
| 6,511,505 | B2 | 1/2003 | Cox et al. | 623/1.16 |
| 6,540,777 | B2 | 4/2003 | Stenzel | 623/1.16 |
| 6,565,598 | B1 * | 5/2003 | Lootz | 623/1.15 |
| 6,579,309 | B1 | 6/2003 | Loos | 623/1.16 |
| 6,579,310 | B1 | 6/2003 | Cox et al. | 623/1.16 |
| 6,582,394 | B1 | 6/2003 | Reiss | 604/96 |
| 6,599,315 | B2 | 7/2003 | Wilson | 623/1.15 |
| 6,602,285 | B1 | 8/2003 | Von Oepen et al. | 623/1.17 |
| 6,663,664 | B1 | 12/2003 | Pacetti | |
| 6,676,987 | B2 | 1/2004 | Zhong et al. | 427/2.24 |
| 6,709,453 | B2 | 3/2004 | Pinchasik et al. | 623/1.15 |
| 6,730,116 | B1 | 5/2004 | Wolinsky et al. | 623/1.15 |
| 6,749,628 | B1 | 6/2004 | Callol | 623/1.15 |
| 6,821,292 | B2 | 11/2004 | Pazienza et al. | 623/1.15 |
| 6,835,203 | B1 | 12/2004 | Vardi | 623/1.16 |
| 6,976,993 | B2 | 12/2005 | Schaldach et al. | |
| 7,144,420 | B2 | 12/2006 | Lenz | 623/1.15 |
| 7,879,084 | B2 | 2/2011 | Goto | |
| 8,157,858 | B2 | 4/2012 | Goto | |
| 2001/0056297 | A1 | 12/2001 | Hojeibane | 623/1.16 |
| 2001/0056298 | A1 | 12/2001 | Brown et al. | 623/1.16 |
| 2002/0004663 | A1 * | 1/2002 | Gittings et al. | 606/153 |
| 2002/0007212 | A1 * | 1/2002 | Brown et al. | 623/1.16 |
| 2002/0035395 | A1 * | 3/2002 | Sugimoto | 623/1.15 |
| 2002/0049487 | A1 | 4/2002 | Lootz et al. | |
| 2002/0055770 | A1 | 5/2002 | Doran et al. | 623/1.15 |
| 2002/0095208 | A1 | 7/2002 | Gregorich et al. | 623/1.15 |
| 2002/0193873 | A1 | 12/2002 | Brucker | 623/1.11 |
| 2003/0018380 | A1 | 1/2003 | Craig et al. | 623/1.15 |
| 2003/0045925 | A1 * | 3/2003 | Jayaraman | 623/1.16 |
| 2003/0158596 | A1 * | 8/2003 | Ikeuchi et al. | 623/1.16 |
| 2003/0195606 | A1 | 10/2003 | Davidson | 623/1.15 |
| 2003/0225449 | A1 | 12/2003 | Denison | |
| 2004/0073290 | A1 | 4/2004 | Chouinard | |
| 2004/0138737 | A1 * | 7/2004 | Davidson et al. | 623/1.35 |
| 2004/0167609 | A1 * | 8/2004 | Majercak | 623/1.15 |
| 2004/0186551 | A1 | 9/2004 | Kao et al. | |
| 2004/0267352 | A1 | 12/2004 | Davidson | 623/1.16 |
| 2004/0267353 | A1 | 12/2004 | Gregorich | 623/1.16 |
| 2005/0010278 | A1 | 1/2005 | Vardi et al. | 606/167 |
| 2005/0038501 | A1 * | 2/2005 | Moore et al. | 623/1.19 |
| 2005/0060027 | A1 | 3/2005 | Khenansho | |
| 2005/0102023 | A1 | 5/2005 | Yadin | 623/1.16 |
| 2005/0131524 | A1 * | 6/2005 | Majercak et al. | 623/1.15 |
| 2005/0131526 | A1 | 6/2005 | Wong | 623/1.15 |
| 2005/0154444 | A1 | 7/2005 | Quadri | 623/1.23 |
| 2005/0228483 | A1 | 10/2005 | Kaplan | 623/1.11 |
| 2006/0036315 | A1 | 2/2006 | Yadin et al. | 623/1.35 |
| 2006/0173528 | A1 * | 8/2006 | Feld et al. | 623/1.15 |
| 2006/0224229 | A1 | 10/2006 | Goto | |
| 2007/0100434 | A1 | 5/2007 | Gregorich et al. | 623/1.16 |
| 2007/0208415 | A1 * | 9/2007 | Grotheim et al. | 623/1.16 |
| 2008/0077228 | A1 | 3/2008 | Goto | |
| 2011/0106239 | A1 | 5/2011 | Goto | |

FOREIGN PATENT DOCUMENTS

| | | |
|---|---|---|
| JP | 2006305341 | 11/2006 |
| WO | 96/26689 | 9/1996 |
| WO | 9965418 | 12/1999 |
| WO | 9965421 | 12/1999 |
| WO | 0003661 | 1/2000 |
| WO | 00/30563 | 6/2000 |
| WO | 01/01889 | 1/2001 |
| WO | 01/08600 | 2/2001 |
| WO | 2007111762 | 10/2007 |

* cited by examiner

STENT WITH OVERLAP AND HIGH EXPANSION

CROSS-REFERENCE TO RELATED APPLICATIONS

This application claims the benefit of and is a continuation-in-part of U.S. patent application Ser. No. 11/392,047, filed Mar. 29, 2006, now U.S. Pat. No. 8,043,358 the entire disclosure of which is incorporated herein by reference.

STATEMENT REGARDING FEDERALLY SPONSORED RESEARCH

Not Applicable.

FIELD OF THE INVENTION

This invention relates to implantable medical devices, such as stents, their manufacture, delivery and methods of use.

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

There remains a need for novel stent designs capable of providing scaffolding support to a vessel bifurcation.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a stent comprises a tubular body having a first region and a second region. The tubular body is defined by a plurality of serpentine bands. Each serpentine band comprises a plurality of alternating proximal turns and distal turns connected by struts. The second region comprises a first serpentine band and a second serpentine band that overlap one another about a common stent circumference. Each serpentine band that is located in the first region of the stent occupies a separate and distinct length portion of the stent.

In at least one embodiment, a stent comprises a tubular body having a first region and a second region. The tubular body is defined by a plurality of serpentine bands. Each serpentine band comprises a plurality of alternating proximal turns and distal turns connected by struts. The second region comprises a first serpentine band and a second serpentine band that overlap one another about a common stent circumference. The first region comprises a serpentine band that is not overlapped by another serpentine band about a common stent circumference.

In at least one embodiment, a stent further comprises a third region, the third region comprising serpentine band that is not overlapped by another serpentine band about a common stent circumference.

In at least one embodiments, a stent further comprises at least one appendage that can be oriented to support the carina of a vessel bifurcation.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
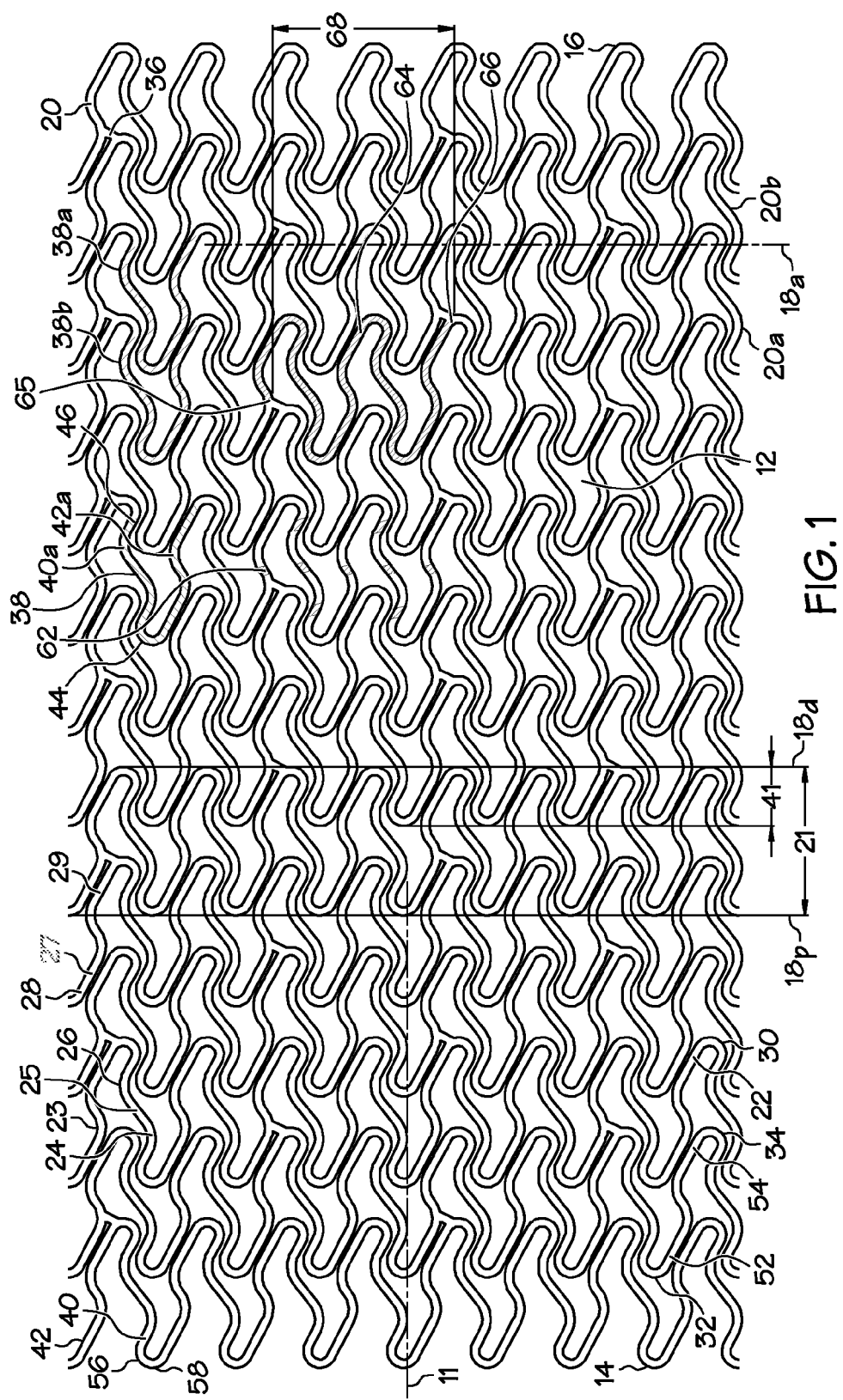
FIG. 1 shows a flat pattern for an embodiment of a stent.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated. Elements depicted in one figure may be combined with, and/or substituted for, elements depicted in another figure as desired.

Figure 2:
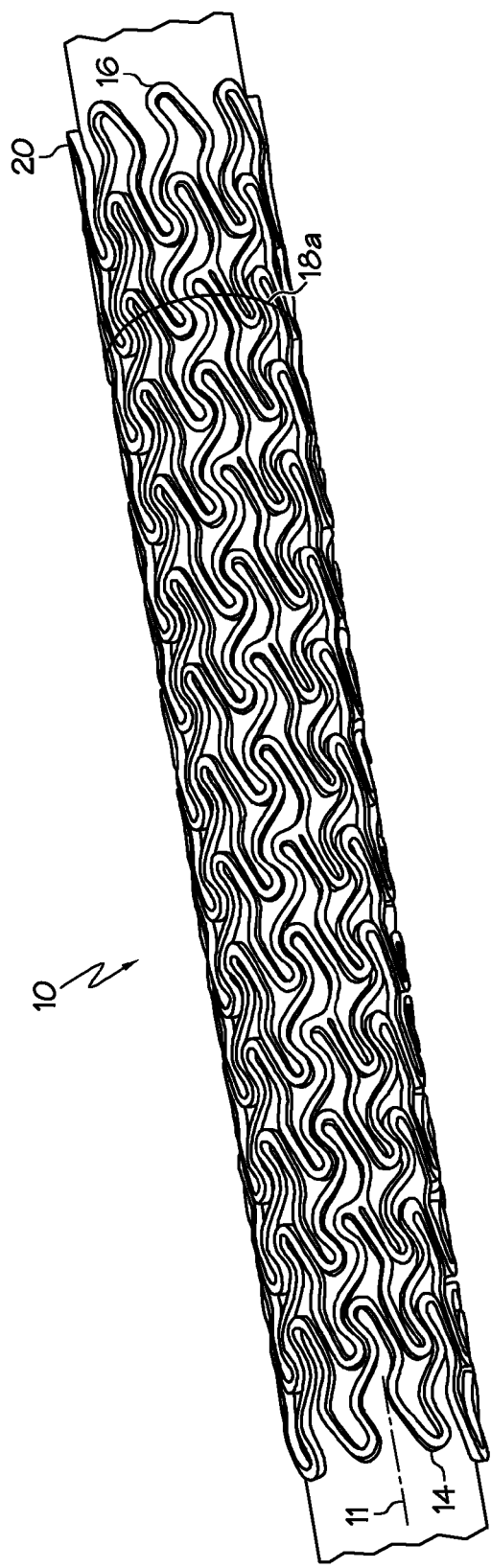
FIG. 2 shows an embodiment of a stent in a substantially unexpanded state.

FIG. 1 shows a flat pattern for an embodiment of a stent 10. FIG. 2 shows a stent 10 according to the pattern depicted in FIG. 1. The stent 10 has a proximal end 14 and a distal end 16, and comprises a plurality of structural elements that define a generally tubular body having a plurality of cells 12. The structural elements further define a plurality of interconnected serpentine bands 20. Adjacent serpentine bands 20 are connected by at least one connector 36.

Each serpentine band 20 comprises a plurality of struts 22 connected by turns 30. Turns 30 may comprise proximal turns 32, located on the proximal side of the serpentine band 20, or may comprise distal turns 34, located on the distal side of the serpentine band 20. Each strut 22 comprises a proximal end 52 that is connected to a proximal turn 32 and a distal end 54 that is connected to a distal turn 54.

Each strut 22 further comprises a curvilinear or serpentine path between its proximal end 52 and distal end 54, and thus includes at least one bend 23. In some embodiments, a strut 22 may comprise multiple bends 23, such as a peak 24 and a valley 26, which may have different orientations. If a peak 24 may be considered convex from a given reference frame, a valley 26 may be considered concave. An inflection point 25 may be located along the curvilinear or serpentine path between a peak 24 and a valley 26.

A valley 26 of a strut 22 may be located closer to the proximal turn 32 to which the strut 22 connects than to the distal turn 34 to which the strut 22 connects. A peak 24 of a strut 22 may be located closer to the distal turn 34 to which the strut 22 connects than to the proximal turn 32 to which the strut 22 connects.

Each strut 22 may further comprise straight portions 27. A straight portion 27 may comprise a proximal straight portion 28 or a distal straight portion 29. A proximal straight portion 28 may be located between the proximal end 52 of the strut 22 and a valley 26. A distal straight portion 29 may be located between a peak 24 and the distal end 54 of the strut 22.

Struts 22 may comprise first struts 40 or second struts 42. First struts 40 may alternate with second struts 42 about a serpentine band 20. Each turn 30 may connect at one end to a first strut 40 and may connect at the other end to a second strut 42. Each turn 30 may further comprise an upper portion 56 and a lower portion 56. It should be understood that "upper" and "lower" as used in this reference frame are relative terms that apply when used in conjunction with a flat pattern stent drawing, and a person of ordinary skill in the art would understand that the relative orientations may change when applied to a three dimensional stent framework of another reference frame.

In some embodiments, a proximal turn 32 upper portion 56 may connect to the proximal end 52 of a first strut 40. A proximal turn 32 lower portion 58 may connect to the proximal end 52 of a second strut 42. A distal turn 34 upper portion 56 may connect to the distal end 54 of a second strut 42. A distal turn 34 lower portion 58 may connect to the distal end 54 of a first strut 40.

All first struts 40 define a similarly shaped curvilinear path. All second struts 42 define a similarly shaped curvilinear path. The curvilinear path defined by the first struts 40 is different from the curvilinear path defined by the second struts 42. A peak 24 and a valley 26 of a second strut 42 may be located closer to one another than a peak 24 and a valley 26 of a first strut 40. The straight portion(s) 27 of a second strut 42 may be longer than the straight portion(s) 27 of a first strut 40. The proximal end 52 of a first strut 40 may be longitudinally and circumferentially offset from the distal end 54, wherein the distal end 54 may be located "above" the proximal end 52 (as depicted in FIG. 1), and the circumferential component of the offset may be oriented in a first direction. The proximal end 52 of a second strut 42 may be longitudinally and circumferentially offset from the distal end 54, wherein the distal end 54 may be located "below" the proximal end 52 (as depicted in FIG. 1), and the circumferential component of the offset may be oriented in a second direction.

The proximal straight portion 28 and the distal straight portion 29 of a first strut 40 may be substantially parallel. A straight portion 27 of a first strut 40 may be parallel to straight portions of other first struts 40, including other first struts 40 included within a common serpentine band 20 and other first struts 40 from different serpentine bands 20. Similarly, the proximal straight portion 28 and the distal straight portion 29 of a second strut 42 may be substantially parallel. A straight portion 27 of a second strut 42 may be parallel to straight portions of other second struts 42, including other second struts 42 included within a common serpentine band 20 and other second struts 42 from different serpentine bands 20. Further, straight portions 27 of first struts 40 may be parallel to straight portions 27 of second struts 42.

All proximal turns 32 included in a serpentine band 20 may be aligned about a common stent circumference $18p$. All distal turns 34 included in a serpentine band 20 may be aligned about another common stent circumference $18d$. Stent circumferences are intended to be oriented orthogonally to a stent central longitudinal axis 11.

All of the peaks 24 of all of the struts 22 of a serpentine band 20 may be substantially aligned along a stent circumference $18p$. The peaks 24 of a serpentine band 20 may further be substantially aligned with the proximal turns 34 of an adjacent serpentine band 20 along a stent circumference 18p. All of the valleys 26 of all of the struts 22 of a serpentine band 20 may be substantially aligned along a stent circumference 18d. The valleys 26 of a serpentine band 20 may further be substantially aligned with the distal turns 34 of an adjacent serpentine band 20 along a stent circumference 18d.

Serpentine bands 20 are oriented such that adjacent serpentine bands 20 overlap one another along the length of the stent 10. Thus, a single common stent circumference 18a may intersect a first serpentine band 20a and a second serpentine band 20b. In some embodiments, there may be enough overlap that the common stent circumference 18a intersects every strut 22 of the first serpentine band 20a and every strut 22 of the second serpentine band 20b. Distal turns 34 of the first serpentine band 20a may be located distal to the common stent circumference 18a, and proximal turns 32 of the second serpentine band 20b may be located proximal to the common stent circumference 18a.

The valleys 26 of struts 22 of a serpentine band 20 may be substantially aligned with the distal turns 34 of an adjacent serpentine band 20 about a stent circumference 18. The peaks 24 of struts 22 of a serpentine band 20 may be substantially aligned with the proximal turns 32 of an adjacent serpentine band 20 about a stent circumference 18.

Each serpentine band 20 may span a band length 21 as measured in a direction parallel to the stent central longitudinal axis 11. Adjacent serpentine bands 20 that overlap may define an overlap length 41 as measured in a direction parallel to the stent central longitudinal axis 11. Various embodiments of a stent 10 may include various amounts of overlap length 41. In some embodiments, the overlap length 41 may be 10%; 15%; 20%; 25%; 30%; 35% or greater than 35% of the band length 21.

Stents 10 made according to the pattern of FIG. 1 are intended to be considered non-helical type stents. The overlap described between adjacent serpentine bands 20 is true when the serpentine bands 20 have a purely circumferential orientation, wherein a circumference of the serpentine band 20 comprises an actual circumference of the stent 10, wherein the actual circumference is oriented orthogonal to the central longitudinal axis 11 of the stent 10.

Each serpentine band 20 may define a plurality of strut pairs 38. A strut pair 38 comprises a first strut 40a and an adjacent second strut 40b that are connected by a turn 30. Thus, a strut pair 38 includes a connected end 44 and an unconnected end 46. In some strut pairs 38, the connected turn 30 may comprise a proximal turn 32. In some strut pairs 38, the connected turn 30 may comprise a distal turn 34.

A portion of a first strut pair 38a of one serpentine band 20 may be nested within a portion of another strut pair 38b of an adjacent serpentine band 20. The connected end 44 of the first strut pair 38a may be nested between the struts 22 of the other strut pair 38b at its unconnected end 46. The overlap or nested area may span from the connected turn 30 to the valleys 26 of the struts 22 of the first strut pair 38a, and may span from the unconnected end 46 to the peaks 24 of the struts 22 of the other strut pair 38b.

Adjacent serpentine bands 20 are connected by at least one connector 36. A connector 36 may span from any suitable location of one serpentine band 20 to any suitable location of another serpentine band 20. In some embodiments, a connector 36 may connect to a turn 30. In some embodiments, a connector 36 may connect to a portion of a strut 22.

The embodiment of a stent 10 shown in FIG. 1 includes connectors 36 that span from a turn 36 of one serpentine band 20 to a strut 22 of an adjacent serpentine band 20. More specifically, connectors 36 span from a distal turn 34 upper portion 56 of one serpentine band 20 to a valley 26 of a strut 22 of an adjacent serpentine band 20.

Connectors 36 may have any suitable size and shape. In some embodiments, the connectors 36 may be considered short when compared to interconnecting elements of prior art stents. In some embodiments, the width of a connector 36 is the same width as other stent elements, such as turns 30 and struts 22. In some embodiments, the width of a connector 36 may be greater than its length.

A serpentine band 20 may define a free strut length 64 between points of connection to other portions of the stent 10, such as a first connection point 65 and a second connection point 66. In some embodiments, connection points 65, 66 are locations where the serpentine band 20 connects to a connector 36. In some embodiments, a first connection point 65 comprises a connection to stent structure located proximal to the serpentine band 20 along the length of the stent 10, and a second connection point 66 comprises a connection to stent structure located distal to the serpentine band 20 along the length of the stent 10. A free strut length 64 may comprise a plurality of struts 22 and a plurality of turns 30, and in some embodiments, may comprise four turns 30 and at least four struts 22. A free strut length 64 may also be described as being an unsupported length of a serpentine band 20 or an unconnected length of a serpentine band 20.

In some embodiments, the total distance traversed along a free strut length 64 between connection points 65, 66 is equal to or greater than a circumference 18 of the stent 10. In various embodiments, this may be true when the stent is in a nominal (i.e. as manufactured or as laser cut) state of expansion and/or when the stent is in a crimped or delivery state of expansion.

The free strut length 64 defines a circumferential length component 68, or distance between connection points 65, 66 as measured in a circumferential direction. A ratio of 'free strut length:circumferential length component' may be described for various free strut lengths 64. In various embodiments, the ratio may be 1:1, 2:1, 7:3, 3:1, 4:1, 5:1 or greater. For the highlighted free strut length 64 depicted in FIG. 1, the ratio is intended to be approximately 4.67:1. For the purposes of measuring free strut length 64 and circumferential length components 68, FIG. 1 may be considered a scale drawing for some embodiments of a stent 10.

A free strut length 64 defines a plurality of inflection zones 62, each inflection zone 62 containing an inflection point 25 wherein the concavity of the serpentine band 20 changes. A free strut length 64 may include any suitable number of inflection zones 62 and in some embodiments may include 5, 7 or 9 or more inflection zones 64. For example, nine inflection zones 62 are marked on an embodiment of a free strut length 64 in FIG. 1.

FIG. 2 shows a stent 10 formed in accordance with the pattern shown in FIG. 1 in a crimped or delivery state. The stent 10 is capable of a high amount of expansion.

Figure 3:
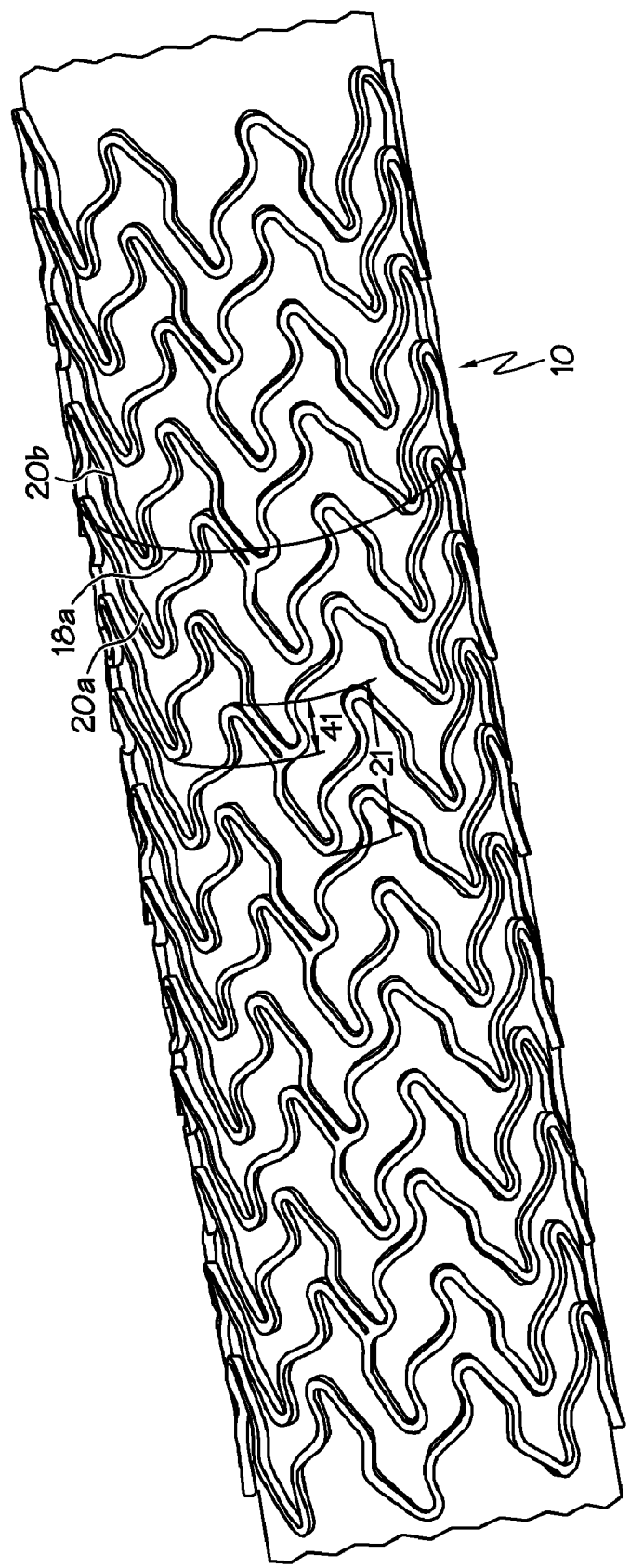
FIG. 3 shows the stent of FIG. 2 in a first state of expansion.

FIG. 3 shows the stent 10 of FIG. 2 in a first expanded state. The diameter of the stent 10 in the first expanded state is approximately 1.9 times the diameter of the stent 10 in the delivery state. Adjacent serpentine bands 20 continue to overlap along the length of the stent 10. A single common stent circumference 18a may continue to intersect a first serpentine band 20a and an adjacent second serpentine band 20b. In some embodiments, there may be enough overlap that the common stent circumference 18a intersects every strut 22 of the first serpentine band 20a and every strut 22 of the second serpentine band 20b.

Figure 4:
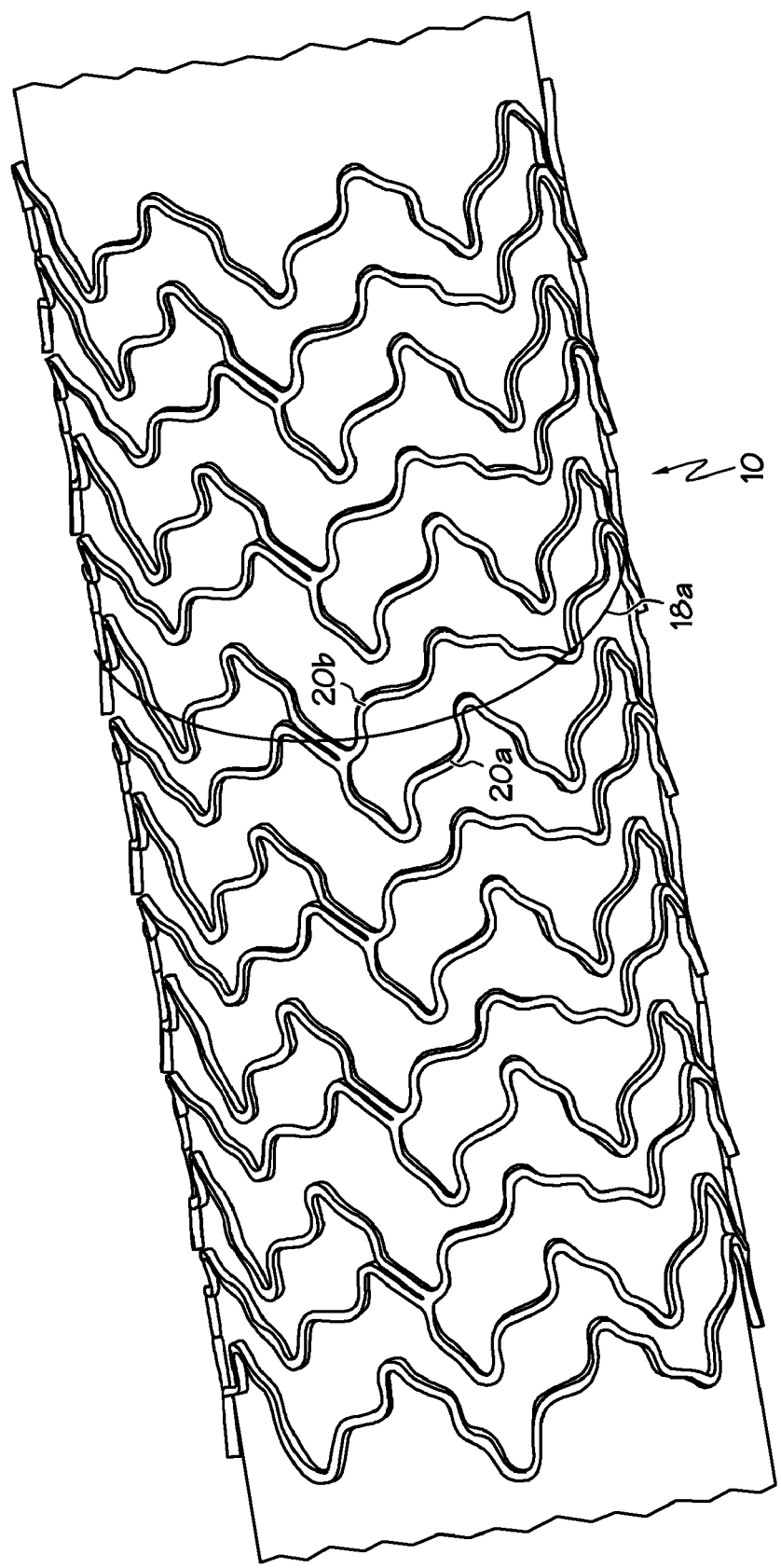
FIG. 4 shows the stent of FIG. 2 in a second state of expansion that is greater than the first state of expansion as shown in FIG. 3.

FIG. 4 shows the stent 10 of FIG. 2 in a second expanded state that is larger than the first expanded state. The diameter of the stent 10 in the second expanded state is approximately 2.7 times the diameter of the stent 10 in the delivery state. Even in the second expanded state, a single common stent circumference 18a may continue to intersect a first serpentine band 20a and an adjacent second serpentine band 20b.

The stent 10 is capable of being expanded far beyond the second expanded state depicted in FIG. 4. A ratio of 'crimped diameter:expanded diameter' is as high as 1:5.1 or greater for some embodiments of the stent 10, with the stent 10 maintaining proper shape and functionality, and the capability of providing adequate scaffolding support to a vessel wall. Thus, the expansion ratios are true without the stent becoming 'over-expanded.' It should be noted that the stents 10 described herein are capable of such expansion with a related axial foreshortening of 10% or less. Further, the stent diameters referred to may generally be considered outer diameters of the stent (i.e. crimped outer diameter:expanded outer diameter), however, in some embodiments, statements made herein may describe the inner diameters (i.e. crimped inner diameter:expanded inner diameter).

The stent 10 is further capable of varying degrees of expansion magnitude along its length. For example, a first portion of the stent 10 may be expanded in accordance with FIG. 4, while a second portion of the stent 10 may be expanded to an even greater degree. The first portion and the second portion may be immediately adjacent to one another along the length of the stent 10. Thus, the stent 10 is particularly useful at a vessel bifurcation.

The stent 10 is also particularly suitable for use in children. As a child ages and bodily vessels grow, a previously implanted stent may require one or more additional expansion operations. The high expansion capability of the stent 10 can allow the stent 10 to be used in situations where a second, larger replacement stent was previously required.

Figure 5:
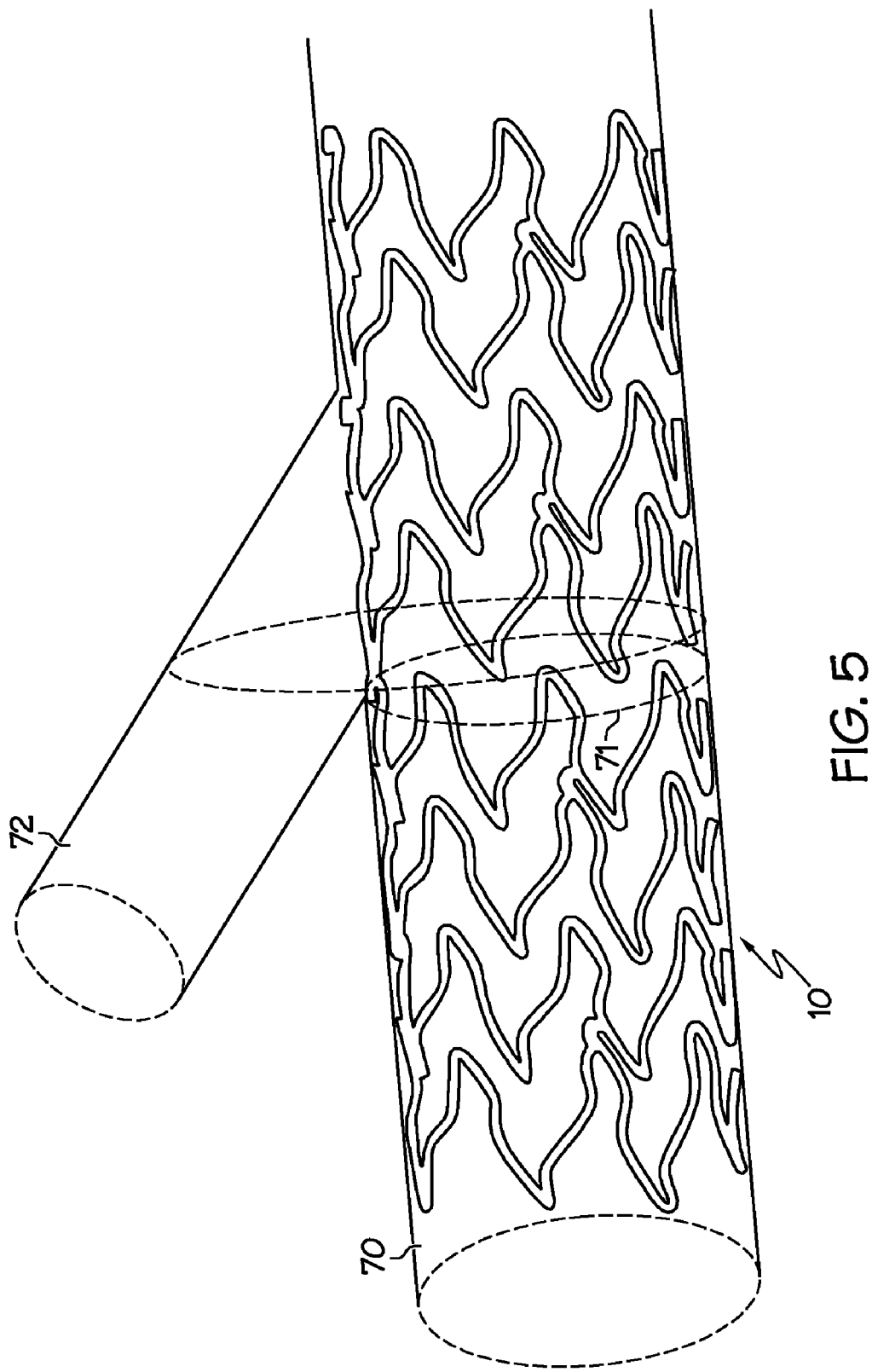
FIG. 5 shows an embodiment of a stent expanded in a vessel.

FIG. 5 shows an embodiment of a stent 10 oriented within a main vessel 70 near a bifurcation. The stent 10 is in a state of expansion roughly equivalent to the second expanded state, for example as shown in FIG. 4. The diameter/size of the stent 10 is approximately equivalent to the diameter/size 71 of the main vessel 70.

Figure 6:
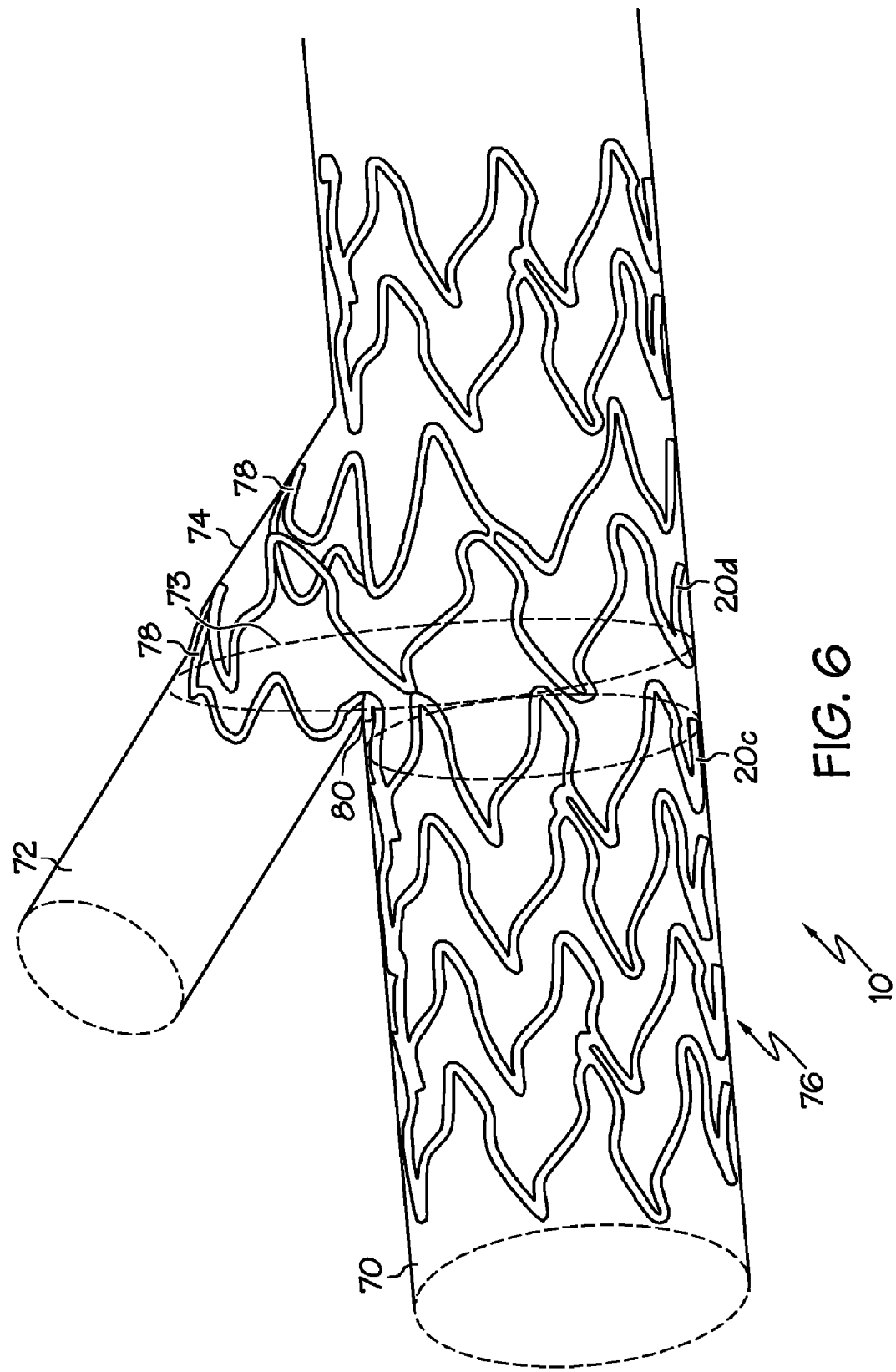
FIG. 6 shows the stent of FIG. 5, wherein a portion of the stent is further expanded into a bifurcation vessel.

The stent 10 includes structure that may be expanded into the side branch vessel 72 to support the side branch vessel 72, for example as shown in FIG. 6. The appropriate structure may be expanded, for example, using a balloon having first and second inflatable portions. The first inflatable portion may be used to expand the main cylindrical framework of the stent 10. The second inflatable portion, which may be inflatable separately from the first inflatable portion, may be used to expand a portion of the stent structure into the side branch vessel 72.

In some embodiments (not shown), a stent 10 may be provided with a side branch opening which may receive a second stent. The stent 10 may be positioned within a main vessel 70 with the side branch opening positioned in proximity to the side branch vessel 72. A second stent may be positioned within the side branch vessel 72 and engaged with the main stent 10.

FIG. 6 shows the stent 10 of FIG. 5, wherein a first portion 76 of the stent 10 remains in the first expanded state and a second portion 78 has been further expanded into the side branch vessel 72. Stent structure extending into the side branch vessel 72 provides support to the contralateral ostial wall 74. The stent 10, in the area of the second portion 78, is expanded to a size 73 greater than that of the main vessel 70. Thus, a first serpentine band 20c may be expanded to a first expanded state in a main vessel 70, and a second serpentine band 20d may be expanded partially into a side branch vessel 72 to a second, larger expanded state, wherein the first serpentine band 20c and the second serpentine band 20d may be immediately adjacent to one another along the length of the stent. A substantial portion of the first serpentine band 20c may be located to one side of the carina 80, while a substantial portion of the second serpentine band 20d may be located to the other side of the carina 80.

Any suitable portion of any serpentine band 20 may be expanded into a side branch vessel 72. Therefore, unlike prior art stents having a specific and dedicated side branch structure, the inventive stents 10 are not required to be placed with any specific rotational orientation with respect to the side branch vessel 72. The stents 10 may simply be placed according to a proper lengthwise orientation, and the serpentine band 20 portions that are consequently oriented with proximity to the side branch vessel 72 may be expanded into the side branch vessel 72. The stents 10 are also suitable for use in vessel locations having more than one bifurcation.

Figure 7:
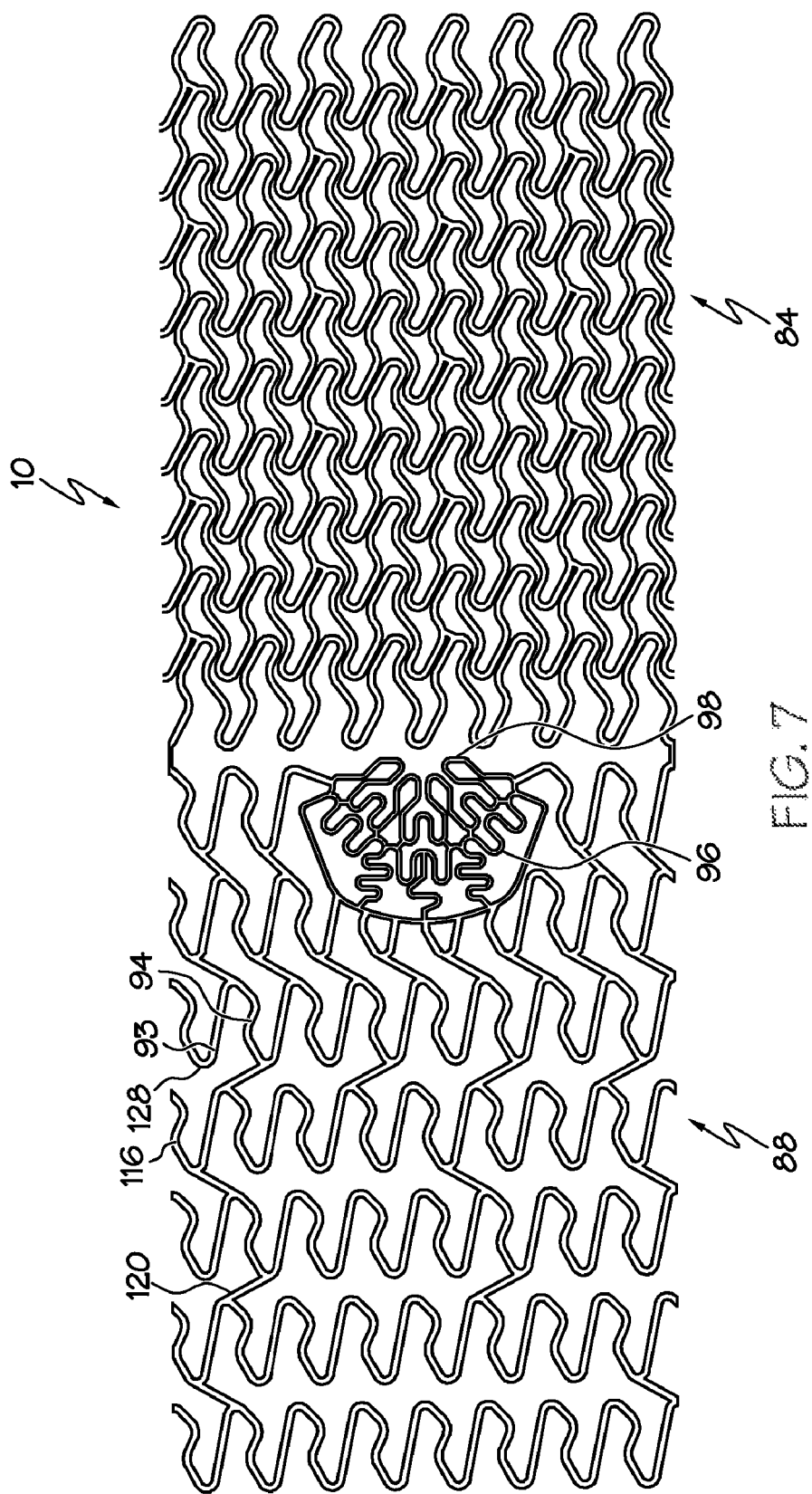
FIG. 7 shows a flat pattern for another embodiment of a stent.

In some instances, a dedicated side branch structure may be desirable. FIG. 7 shows a flat pattern for an embodiment of a stent 10 comprising a first portion 84 and a second portion 88. The first portion 84 may comprise overlapping serpentine bands 20 and stent structure as described herein, for example with respect to FIG. 1. The second portion 88 may comprise any suitable stent structure and a partial side branch structure 96.

The stent structure of the second portion 88 may comprise a pattern of serpentine bands 116 and connector struts 120. The serpentine bands 116 may comprise alternating straight struts 93 and s-shaped struts 94 connected by turns 128, for example as described with respect to various stent embodiments disclosed in U.S. patent application Ser. No. 11/262,692, the entire disclosure of which is hereby incorporated herein by reference in its entirety.

The partial side branch structure 96 may comprise any suitable stent side branch structure and in some embodiments may comprise a plurality of outwardly deployable petal structures 98. Examples of stent side branch structure are described, for example, in U.S. Patent Application Publication No. 20050060027, the entire disclosure of which is hereby incorporated herein by reference in its entirety.

The partial side branch structure 96 may be considered a "partial" structure because it is not intended to support a full 360 degrees of the side branch vessel, and thus, the partial side branch structure 96 is reduced from the "full" side branch structures generally shown in the prior art. As depicted in FIG. 7, the partial side branch structure 96 extends approximately 180 degrees, and may thus be considered a half-crown structure.

When the stent 10 of FIG. 7 is expanded at a vessel bifurcation, the first portion 84 may extend into a side branch vessel 72 and support the contralateral ostial wall 74 (see FIG. 6). The partial side branch structure 96 may unfold into the side branch vessel 72 in proximity to the carina 80. Therefore, the first portion 84 of the stent 10 supports a first portion of the side branch vessel 72, and the partial side branch structure 96 supports a second portion of the side branch vessel 72, with each portion 84, 96 providing approximately half of the total support provided to the side branch vessel 72. Thus, a ratio of first portion 84 support to partial side branch structure 96 support is approximately 50:50. Various embodiments of stents 10 may include any suitable division between the amount of support provided to the side branch vessel 72 by each portion 84, 96. For example, various embodiments of stents 10 may have support ratios of 55:45, 60:40, 65:35, 70:30, etc., as well as 45:55, 40:60, 35:65, 30:70, etc.

In various embodiments of a stent 10, the stent pattern of the first portion 84 may comprise more of the total stent structure or less of the total stent structure than depicted in FIG. 7. For example, in some embodiments, the first portion 84 may comprise two or three serpentine bands 20 being located immediately adjacent to the partial side branch structure 96. Desirably, the stent axial length spanned by the first portion 84 is equal to or greater than the stent axial length spanned by the partial side branch structure 96. In some embodiments, a stent 10 may include the structure of the second portion 88 on both proximal and distal sides of the first portion 84. Further, the pairing of the partial side branch structure 96 and the first portion 88 may be located anywhere along the length of the stent 10, and in some embodiments is substantially centered as shown in FIG. 7.

Figure 8:
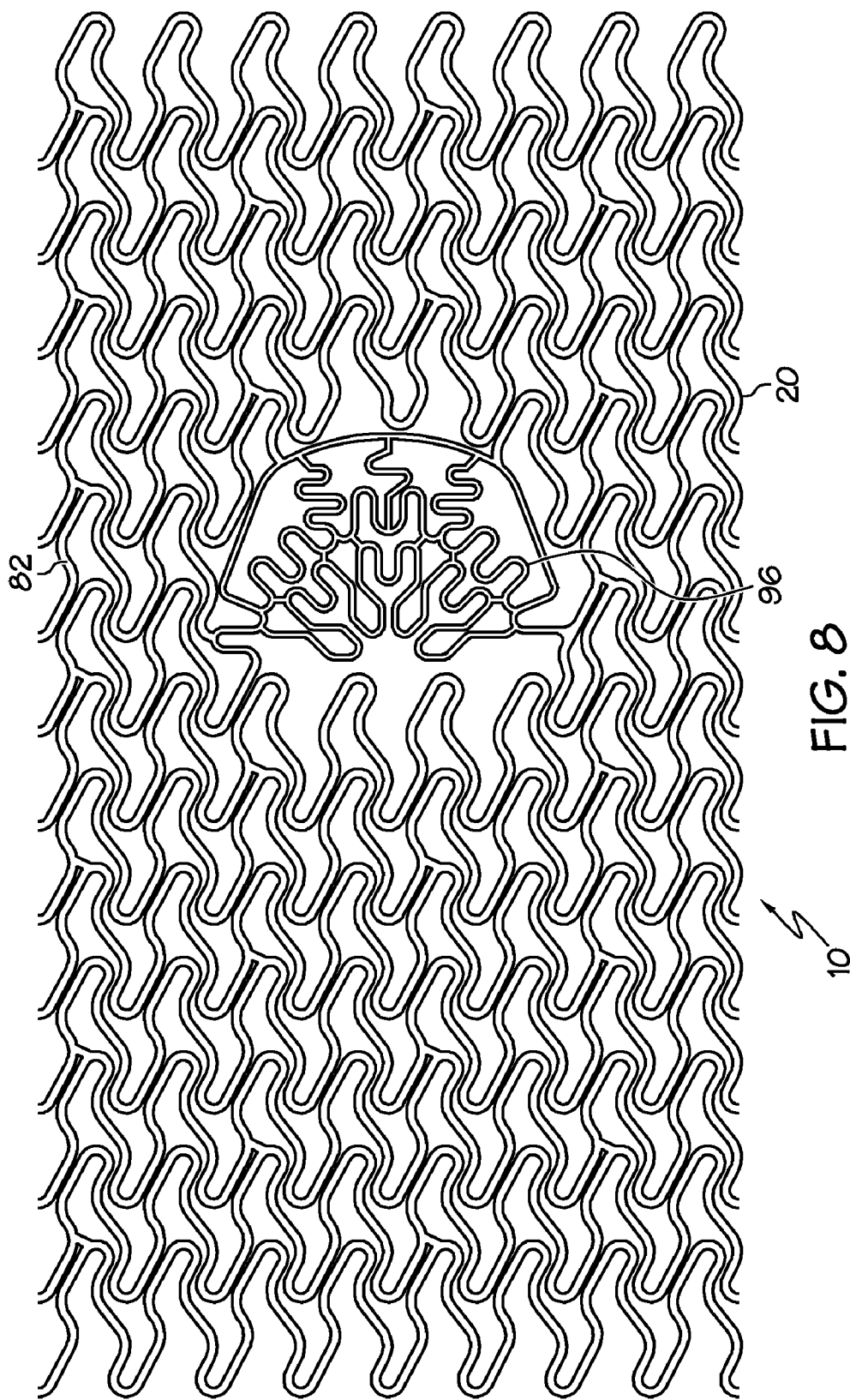
FIG. 8 shows a flat pattern for another embodiment of a stent.

FIG. 8 shows a flat pattern for another embodiment of a stent 10. The stent 10 comprises a plurality of serpentine bands 20 as described herein, for example with respect to FIG. 1. The stent 10 further comprises a partial side branch structure 96 and at least one partial serpentine band 82. A partial serpentine band 82 does not extend about the entire circumference of the stent 10, and generally connects with the partial side branch structure 96.

Stent structure may be expanded into a side branch vessel using any suitable method. In some embodiments, a balloon having a second expandable portion, for example as described in U.S. Patent Application Publication No. 20050060027, may be used to expand either or both of the second portion 78 (see FIG. 6) and the partial side branch structure 96. Self-expanding embodiments are also desirable in that they will automatically expand into the side branch vessel.

Figure 9:
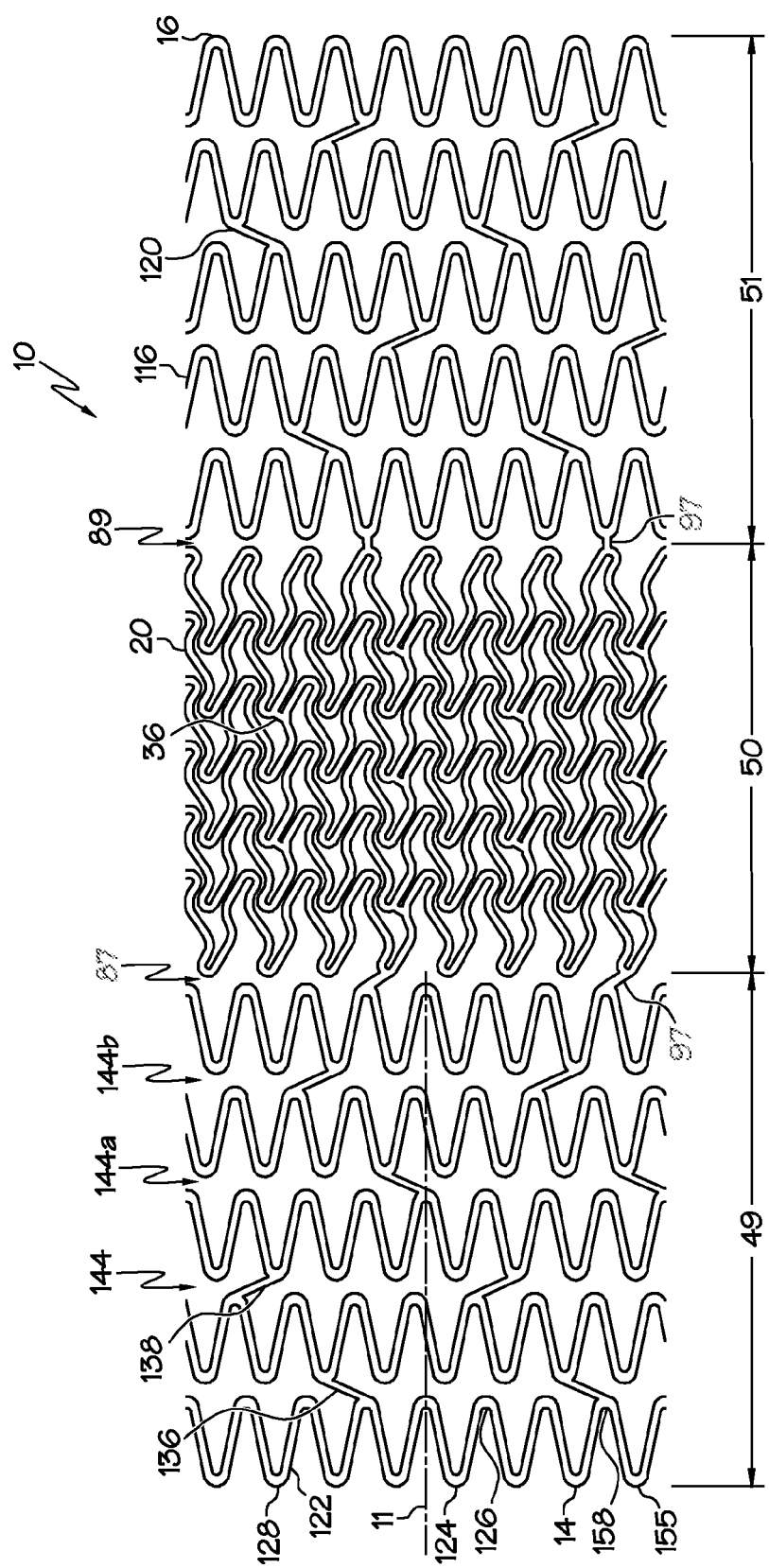
FIG. 9 shows a flat pattern for another embodiment of a stent.

FIG. 9 shows a flat pattern for another embodiment of a stent 10, wherein the end regions are provided with a different structural framework pattern than the central region. In some embodiments, a stent 10 comprises a first portion 49, a second portion 50 and a third portion 51. Each portion 49, 50, 51 can occupy a distinct length portion of the stent 10. For example, the second portion 50 can comprise a central region. The first portion 49 can span from the proximal end 14 of the stent 10 to the second portion 50. The third portion 51 can span from the second portion 50 to the distal end 16 of the stent 10.

In some embodiments, the first and third portions 49, 51 can comprise stent structure that is different from the stent structure of the second portion 50. For example, the first and third portions 49, 51 can each comprise serpentine bands 116 that are spaced apart from one another, and the second portion 50 can comprise serpentine bands 20 that overlap one another. In some embodiments, each serpentine band 116 located in the first and third portions 49, 51 occupies a separate and distinct length portion of the stent 10.

Desirably, the second portion 50 comprises serpentine bands 20 and connectors 36 having high expansion capability as described herein, for example with respect to FIG. 1.

The first portion 49 and the third portion 51 can each comprise any suitable stent structure. In some embodiments, the first and third portions 49, 51 can be shaped similar to one another. In some embodiments, the first and third portions 49, 51 can be different from one another.

In some embodiments, the first portion 49 and/or the third portion 51 can comprise a plurality of serpentine bands 116 and a plurality of connector struts 120. Each serpentine band 116 comprises a plurality of band struts 122 and a plurality of turns 128. The band struts 122 and the turns 128 can alternate as the serpentine band 116 is traversed. The turns 128 can comprise alternating proximal peaks 124 and distal valleys 126. Each proximal peak 124 is generally convex with respect to the proximal end 14 of the stent 10 and concave with respect to the distal end 16 of the stent 10. Each distal valley 126 is generally convex with respect to the distal end 16 of the stent 10 and concave with respect to the proximal end 14 of the stent 10.

Each portion 49, 51 can have any suitable number of serpentine bands 116. In various embodiments, a serpentine band 116 can have any suitable number of band struts 122 and any suitable number of turns 128. Each serpentine band 116 can span any suitable distance along the length of the stent 10. In some embodiments, a stent 10 can comprise serpentine bands 116 that span different distances. One method for increasing a lengthwise span of a serpentine band 116 is to increase the length of the band struts 122.

Serpentine bands 116 that are adjacent to one another along the length of a portion 49, 51 are connected by at least one connector strut 120. In some embodiments, a connector strut 120 spans between turns 128 of adjacent serpentine bands 116. In some embodiments, connector struts 120 can comprise a first type of connector strut 136 and a second type of connector strut 138. A first connector strut 136 extends in a first direction. The first connector strut 136 can be oriented at a first angle to a stent lengthwise axis 11. A second connector strut 138 extends in a second direction that is different from or non-parallel to the first direction. The second connector strut 138 can be oriented at a second angle to a stent lengthwise axis 11.

In some embodiments, an area of a portion 49, 51 located between two adjacent serpentine bands 116 can be considered a connector column 144. Each connector column 144 comprises a plurality of connector struts 120. In some embodiments, each connector strut 120 in a connector column 144 can be similar to one another. For example, each connector strut 120 in a first connector column 144a can comprise a first type of connector strut 136. Each connector strut 120 in a second connector column 144b can comprise a second type of connector strut 138. In some embodiments, first connector columns 144a and second connector columns 144b can alternate along the length of the portion 49, 51.

Turns 128 can comprise connected turns 158 or unconnected turns 155 depending upon whether the turn 128 connects to a connector strut 120.

Other examples of possible stent structure suitable for use in either portion 49, 51 are disclosed in U.S. Patent Application Publication No. 2002/0095208 and U.S. patent application Ser. No. 11/262,692.

The stent 10 further comprises a first transition region 87 between the first portion 49 and the second portion 50, and a second transition region 89 between the second portion 50 and the third portion 51. Each transition region 87, 89 can include at least one transition connector 97 that connects to stent structure on either side of the region 87, 89. For example, a transition connector 97 in the first transition region 87 can be connected at one end to stent structure of the first portion 49, and can be connected at the other end to stent structure of the second portion 50.

In some embodiments, either transition region 87, 89 can comprise a single transition connector 97. In some embodiments, a transition region 87, 89 can comprise a plurality of transition connectors 97.

In some embodiments, a transition connector 97 in the first transition region 87 can comprise the same shape as a transition connector 97 in the second transition region 89. In some embodiments, one or more transition connectors 97 in the first transition region 87 can comprise a shape that is different from the shape of a transition connector 97 in the second transition region 89.

In some embodiments, a transition connector 97 can be straight along its length. In some embodiments, a transition connector 97 can be oriented at an angle to the stent longitudinal axis 11.

Figure 13:
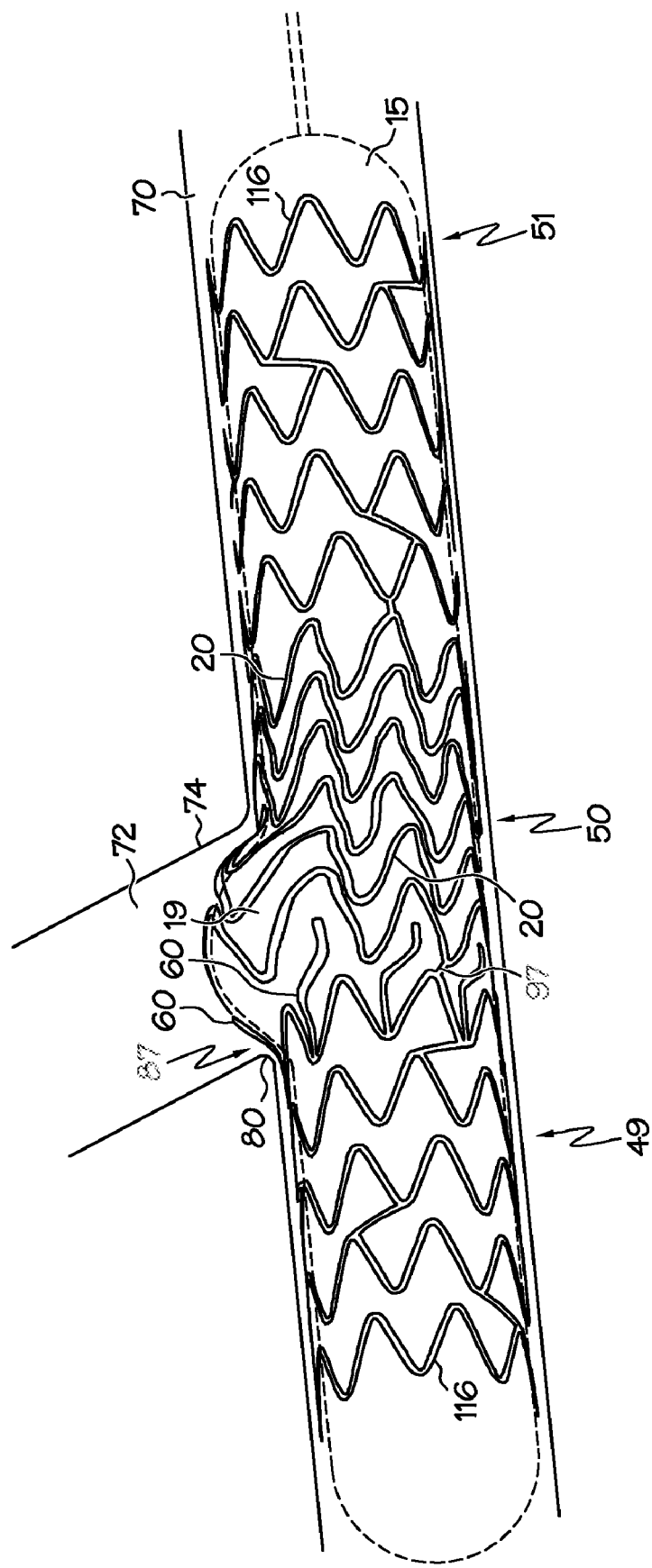
FIG. 13 shows an embodiment of a stent being expanded at a vessel bifurcation.
Figure 14:
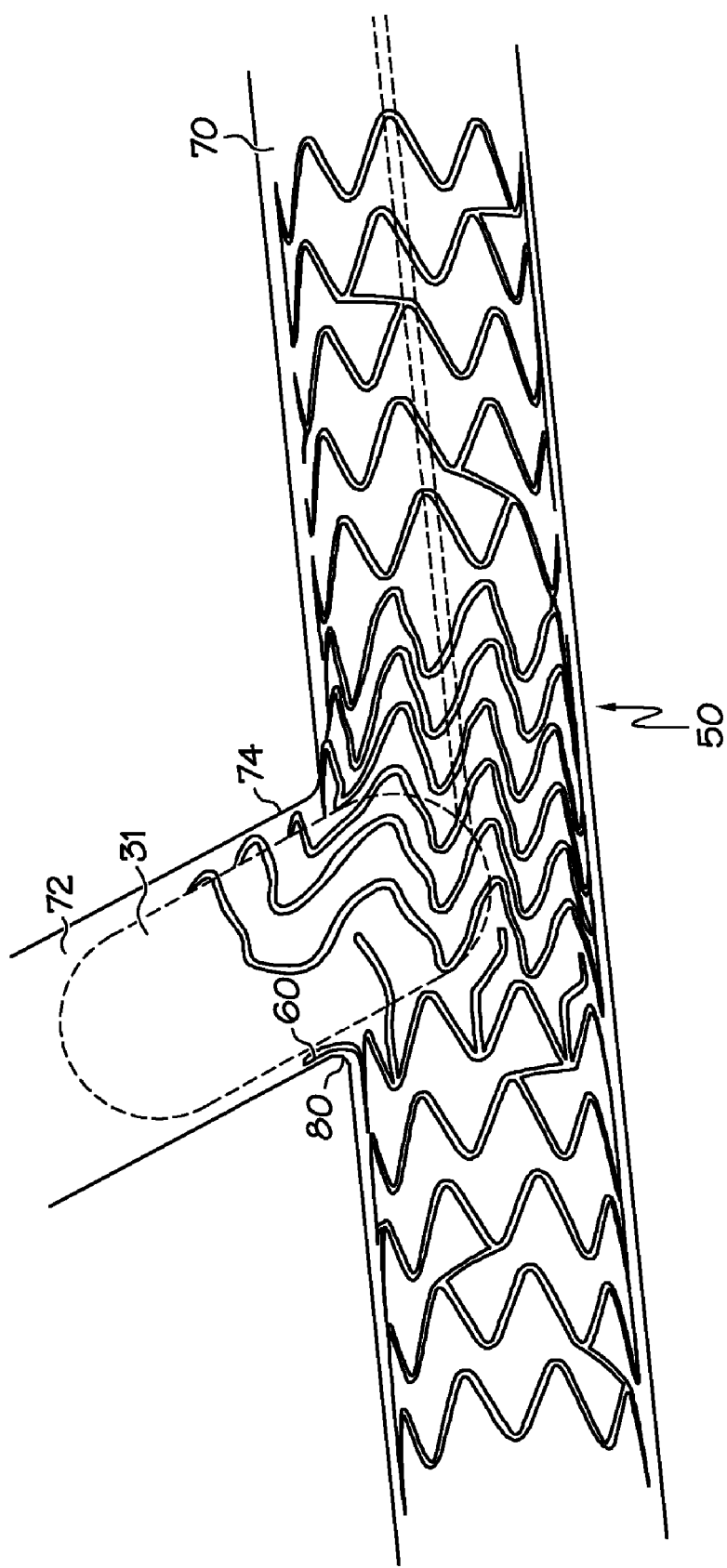
FIG. 14 shows the stent of FIG. 13 at another stage of expansion.

The stent 10 shown in FIG. 9 can be deployed at a vessel bifurcation, for example as shown in FIGS. 13 and 14. The serpentine bands 20 of the second portion 50 are designed with overlap along the length of the stent 10 and a relatively long unsupported strut length. Therefore, the serpentine bands 20 of the second portion 50 are capable of expanding into a branch vessel 72 and simultaneously supporting both the main vessel 70 and the branch vessel 72, for example supporting the contralateral ostial wall 74.

The serpentine bands 116 of the first and third portions 49, 51 comprise a structural pattern that is more conventional than that of the second portion 50. Generally, the structure of the first and third portions 49, 51 provides a greater resistance to radial deformation than the second portion 50, but is capable of a lesser degree of expansion. Therefore, the second portion 50 is constructed and arranged to expand into the side branch vessel 72, while the first and second portions 49, 51 provide a greater strength to support the main vessel 70 on either side of the vessel bifurcation.

Figure 10:
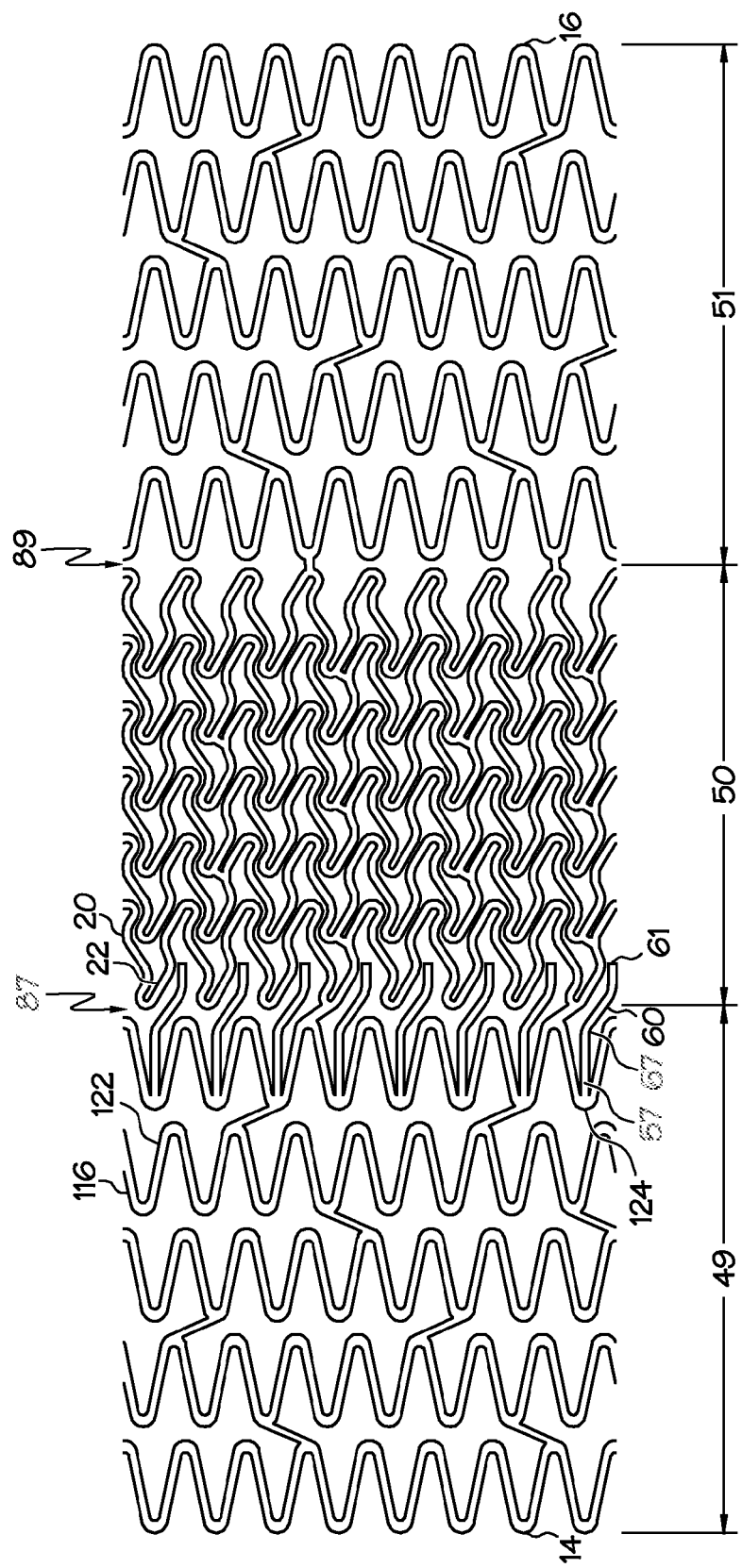
FIG. 10 shows a flat pattern for another embodiment of a stent.

FIG. 10 shows a flat pattern for another embodiment of a stent 10 having a second portion 50 that comprises a structural framework pattern that is different from the first and third portions 49, 51. In some embodiments, the stent 10 further comprises a plurality of appendages 60. The appendages 60 can be constructed and arranged to support the carina of a vessel bifurcation, such as described below with respect to FIGS. 13 and 14.

In some embodiments, an appendage 60 comprises an unsupported or free end 61. In some embodiments, an appendage 60 is connected at a connected end 57 to a serpentine band 116, for example a serpentine band 116 of the first portion 49, and is unsupported along its length. Thus, in some embodiments, an appendage 60 can connect to other stent framework only at a single connected end 57, and can comprise a cantilever type structure.

An appendage 60 can be located in a transition region 87, 89. In some embodiments, a stent 10 includes appendages 60 in the first transition region 87 as shown in FIG. 10. In some embodiments, a stent 10 can include appendages 60 in both the first and second transition regions 87, 89.

In some embodiments, an appendage 60 can be connected to a serpentine band 116 of the first portion 49 and extend into the second portion 50. In some embodiments, appendages 60 and struts 22 of at least one serpentine band 20 of the second portion 50 can overlap about a common stent circumference. In some embodiments, an appendage 60 is connected at a connected end 57 to a proximal peak 124 of a serpentine band 116 of the first portion 49, and extends across the first transition region 87 toward the distal end 16 of the stent 10.

In some embodiments, an appendage 60 can be straight. In some embodiments, an appendage 60 can include curvature, for example comprising a bend 67. In some embodiments, an appendage 60 can comprise multiple bends 67. In some embodiments, an appendage 60 can comprise one or more portions that are oriented parallel to the stent longitudinal axis 11. In some embodiments, an appendage 60 can comprise at least one portion that is oriented at an angle to the stent longitudinal axis 11.

In some embodiments, the width of an appendage 60 is constant along its length. In some embodiments, the width of an appendage 60 can be approximately equal to the width of a strut 22, 122 of a serpentine band 20, 116 of the stent 10. In some embodiments, the width of an appendage 60 can be close to the width of a strut 22, 122 of a serpentine band 20, 116 of the stent 10, for example comprising 80-120% of the strut width.

In some embodiments, an appendage 60 can comprise a material that is more radiopaque that other portions of the stent 10, for example comprising a radiopaque marker. Radiopaque appendages 60 can aid in stent placement.

Figure 11:
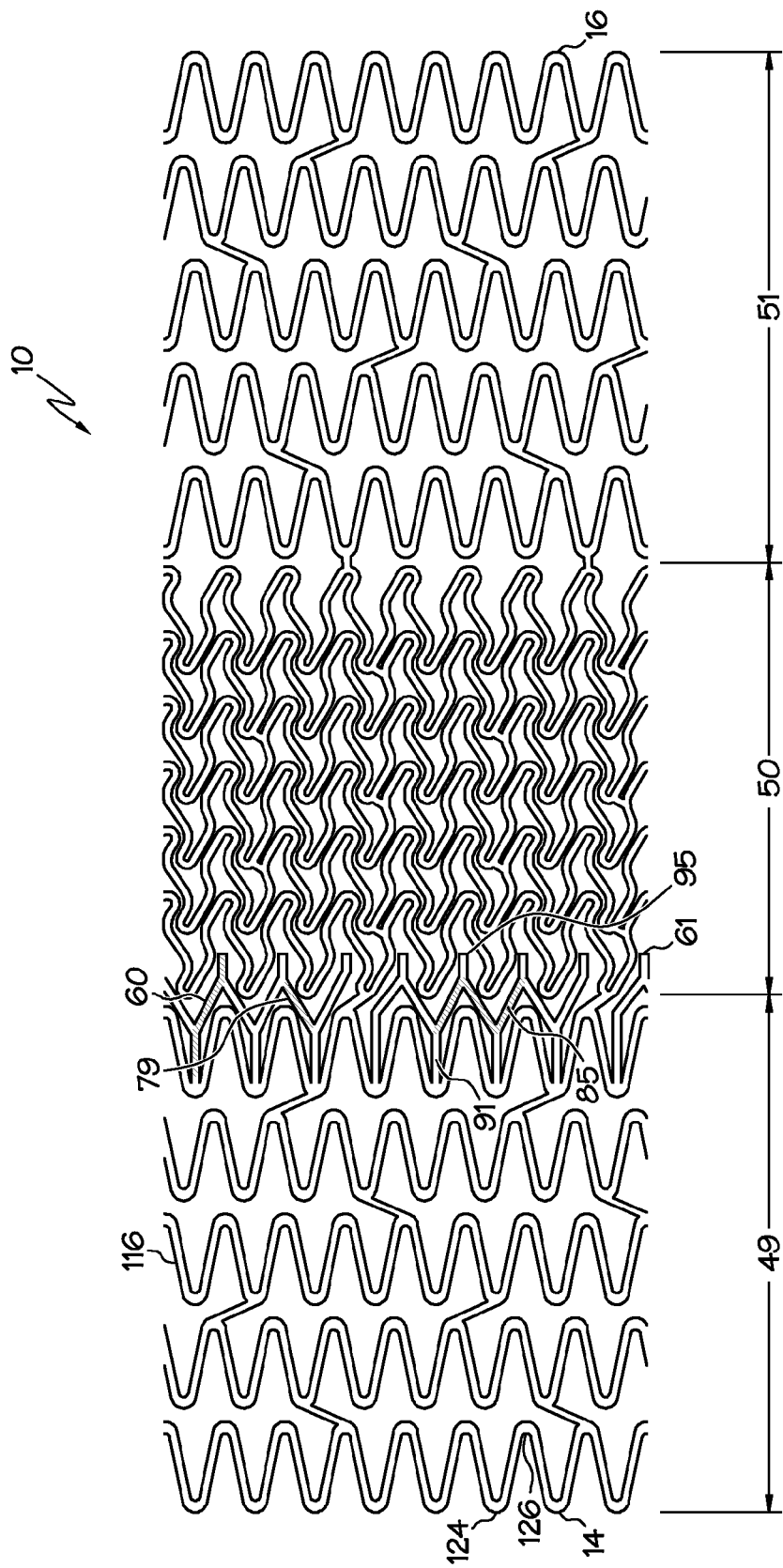
FIG. 11 shows a flat pattern for another embodiment of a stent.

FIG. 11 shows a flat pattern for another embodiment of a stent 10 having a second portion 50 that comprises a structural framework pattern that is different from the first and third portions 49, 51. In some embodiments, the stent 10 further comprises a plurality of appendages 60. In some embodiments, the stent 10 further comprises a plurality of linking members 79 that span between appendages 60. In some embodiments, a linking member 79 is connected at one end to an appendage 60 and is connected at the other end to a circumferentially adjacent appendage 60.

A linking member 79 can be located in a transition region 87, 89. In some embodiments, linking members 97 can brace the appendages 60 against deformation, such as deformation in a tangential direction during stent expansion/deployment.

In some embodiments, the appendage structure can comprise a serpentine structure 85. In various embodiments, peaks and valleys of the serpentine structure 85 can be angular or curved, and the serpentine structure 85 can comprise a waveform or a zig-zag type structure. The appendage structure can further include connecting struts 91 and appendage tip struts 95. A connecting strut 91 can connect the serpentine structure 85 to stent structure that is located outside of the second portion 50, such as a serpentine band 116 of the first portion 49. In some embodiments, a connecting strut 91 can be connected at one end to a proximal peak 124 of a serpentine band 116, and can be connected at the other end to the serpentine structure 85. An appendage tip strut 95 can be connected to the serpentine structure 85 and can further comprise a free end 61.

Figure 12:
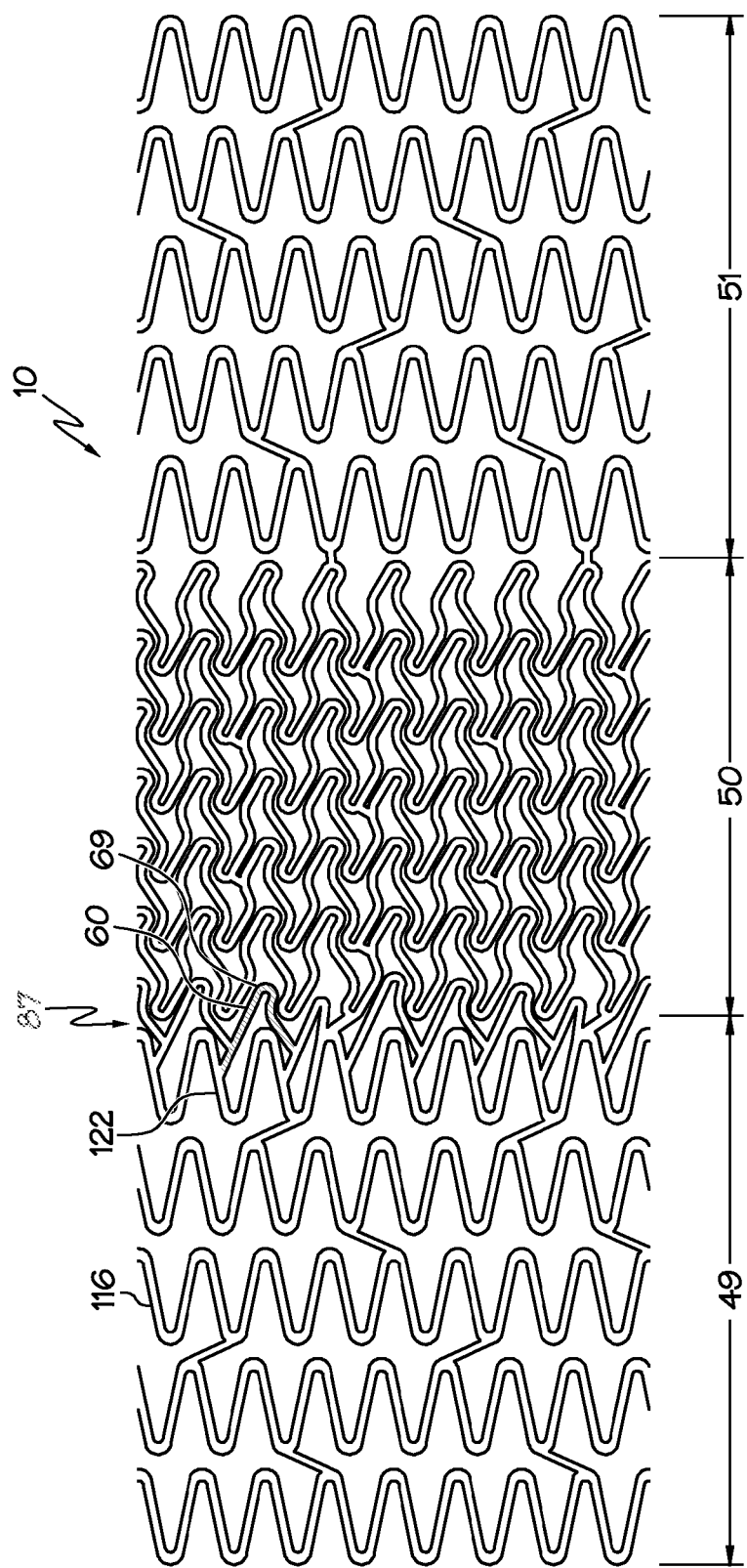
FIG. 12 shows a flat pattern for another embodiment of a stent.

FIG. 12 shows a flat pattern for another embodiment of a stent 10 having a second portion 50 that comprises a structural framework pattern that is different from the first and third portions 49, 51. In some embodiments, an appendage 60 can comprise a peak 69. In some embodiments, an appendage 60 can be connected at one end to a serpentine band 116, such as a strut 122 of a serpentine band 116 located in the first portion 49. The appendage 60 can extend across the first transition region 87 into the second portion 50 and loop back through the first transition region 87 and extend back into the first portion 49. The second end of the appendage 60 can then connect to other stent structure, such as the serpentine band 116, a circumferentially adjacent appendage 60, etc.

FIG. 13 shows an embodiment of a stent 10 oriented in a vessel bifurcation during an expansion operation. The stent 10 can be placed in a main vessel 70 with the second portion 50 aligned with the branch vessel 72. Desirably, for example when the stent 10 comprises appendages 60, the first transition region 87 can be placed in longitudinal alignment with the carina 80 of the bifurcation. Desirably, the first portion 49 of the stent 10 can be located proximal to the bifurcation, and the third portion 51 of the stent 10 can be located distal to the bifurcation.

The stent 10 can be expanded in the main vessel 70 using any suitable method, such as an inflation balloon 15. In some embodiments, the inflation balloon 15 can comprise a raised portion 19 capable of expanding the serpentine bands 20 of the second portion 50 into the branch vessel 72. When the stent 10 includes appendages 60, desirably the balloon 15 will also expand one or more appendages 60 into the branch vessel 72. An example of a balloon having a raised portion is disclosed in U.S. 20060036315, the entire disclosure of which is hereby incorporated herein by reference. Other examples of suitable balloons, such as balloons having a secondary inflatable portion, are disclosed in U.S. 20050060027, mentioned previously herein. In some embodiments, a balloon 15 can comprise a compliant balloon. In some embodiments, a balloon 15 can comprise a non-compliant balloon with a compliant outer layer or surrounding compliant balloon, wherein the non-compliant portion expands the stent 10 in the main vessel 70, and the compliant layer or portion is further expanded to expand the serpentine bands 20 into the branch vessel 72. In some embodiments, a balloon 15 can comprise a semi-compliant balloon having a portion that will expand into the branch vessel 72. After the expansion depicted in FIG. 13 is performed, the balloon 15 can be removed.

FIG. 14 shows the stent 10 of FIG. 13 in a further state of expansion. In some embodiments, after expansion as described with respect to FIG. 13, a guidewire can be placed through the bifurcation into the branch vessel and used to guide a second balloon 31 into the bifurcation. In various embodiments, a second balloon 31 can be a compliant balloon or a non-compliant balloon. In some embodiments, the second balloon 31 can be provided with a second stent (not shown) that will be used to support the branch vessel 72.

The second balloon 31 can be inflated, expanding serpentine bands 20 of the second portion 50 further into the branch vessel 72 and against the contralateral ostial wall 74. The second balloon 31 can also form the appendages 60 around the carina 80, thereby providing stent support to the carina 80.

In some embodiments, a stent 10 can be crimped or reduced to a delivery size with a portion of a serpentine band 20 overlaying an appendage 60 in a stent radial direction. Thus, a serpentine band 20 can be used to overlay and protect the appendages 60 during stent delivery. In some embodiments, the size of a stent 10 can be reduced in a two step process. First, the first portion 49 of the stent 10, along with the appendages 60, can be reduced in size. Next, the remaining portions of the stent 10, including the second portion 50, can be reduced in size. In some embodiments, portions of the serpentine band 20 nearest the first transition region 87 will overlay portions of appendages 60.

In some embodiments, a stent 10 can be self-expanding, for example being made from a shape-memory material such as nickel titanium.

When a self-expanding stent 10 comprises different serpentine band 20, 116 patterns in different regions 49, 50, 51, for example as shown in FIGS. 9-12, the serpentine bands 20 in the second region 50 can be arranged to self-expand to a larger size than the serpentine bands 116 of the end regions 49, 51. For example, the serpentine bands 116 of either end region 49, 51 can be heatset to expand to a nominal expanded diameter d, and the serpentine bands 20 of the second region 50 can be heatset to expand to a larger diameter such as 1.1 d; 1.25 d; 1.5 d; 1.75 d; 2 d; etc. Thus, the second region 50 is capable of expanding into a branch vessel.

The invention is further directed to methods of delivering stents 10 as described herein to a deployment site, and to expanding the stent structure within a main branch vessel and into a side branch vessel, as would be understood by a person of ordinary skill in the art.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

When a stent 10 comprises different serpentine band 20, 116 patterns in different regions 49, 50, 51, for example as shown in FIGS. 9-12, the second region 50 can have a denser strut pattern, and therefore a greater amount of structural material in a unit of area then the end regions 49, 51. Therefore, it can be desirable to apply a greater amount of therapeutic agent to the regions that are less dense.

It can also be desirable to provide various areas within a region 49, 50, 51 with varying amounts of therapeutic agent. For example, localized areas of the second region 50, such as areas that are expected to extend into a branch vessel 72, can include a greater concentration of therapeutic agent.

In some embodiments, a stent 10 can comprise reservoirs that can be filled with a therapeutic agent. Reservoirs, pits and/or other suitable areas can be formed in a stent, for example, by etching and/or laser ablation. The reservoirs can then be filled using any suitable technique.

In some embodiments, a therapeutic agent can be applied using an Anilox rolling technique. Anilox rollers are described, for example, in U.S. Pat. No. 5,989,639; U.S. Pat. No. 6,006,665; and U.S. Pat. No. 6,312,367; the entire disclosures of which are hereby incorporated herein by reference.

In some embodiments, a therapeutic agent can be applied using a machine available from Microdrop Technologies GmbH, Muehlenweg 143, D-22844 Norderstedt, Germany, such as their AD, MD or MJ series dispenser systems.

In some embodiments, a therapeutic agent can be applied using a machine available from Labcoat Limited, Ballybrit Business Park, Unit 4, Galway, Ireland, such as a machine suitable for their proprietary Juxtaposed Ablumenal (JA™) Coating & Process technology.

In some embodiments, a therapeutic agent can be applied using inkjet printer technology. In some embodiments, a therapeutic agent can be applied according to methods disclosed in U.S. Pat. No. 6,676,987, the entire disclosure of which is hereby incorporated herein by reference.

In some embodiments, a therapeutic agent can be applied using a direct writing technique, for example as described in U.S. Pat. No. 4,485,387, the entire disclosure of which is hereby incorporated herein by reference. Direct writing devices are available, for example, from Ohmcraft, Inc., 93 Paper Mill Street, Honeoye Falls, N.Y. 14472.

In some embodiments, one layer of a therapeutic agent can be applied to the second portion 50, and multiple layers can be applied to the first and third portions 49, 51.

In some embodiments, a radiopaque material can be applied to portions of the stent 10, such as the appendages 60. In some embodiments, both radiopaque material and therapeutic agent(s) can be applied to the stent 10. For example, engraved cells of an Anilox roller can be provided with alternating therapeutic agent and radiopaque material, and both can be applied to localized areas of the stent 10.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A stent having a proximal end and a distal end, the stent comprising:
   a tubular body, the tubular body comprising a first region, a second region and a third region, each region of the tubular body defined by a plurality of serpentine bands, each serpentine band comprising a plurality of alternating proximal turns and distal turns connected by struts, at least one serpentine band of the first region shaped differently from a serpentine band of the second region;
   the second region comprising a first serpentine band and a second serpentine band that overlap one another about a common stent circumference, at least one strut of the first serpentine band having a serpentine shape, at least one strut of the second serpentine band having a serpentine shape, the first serpentine band and the second serpentine band each comprising alternating first and second struts, the first struts shaped differently from the second struts, all proximal turns of the first serpentine band aligned about a common stent circumference, all distal turns of the first serpentine band aligned about a common stent circumference, all proximal turns of the second serpentine band aligned about a common stent circumference, all distal turns of the second serpentine band aligned about a common stent circumference; and
   the first region and the third region each comprising a plurality of serpentine bands that are not overlapped by another serpentine band.

2. The stent of claim 1, wherein the struts of the first serpentine band and the struts of the second serpentine band overlap about a common stent circumference.

3. The stent of claim 1, wherein none of the serpentine bands in the first region or the third region overlap one another.

4. The stent of claim 1, wherein each serpentine band in the second region is overlapped by at least one other serpentine band.

5. The stent of claim 1, the second region further comprising a third serpentine band, wherein the second serpentine band and the third serpentine band overlap one another about a common stent circumference.

6. The stent of claim 1, the first region comprising alternating serpentine bands and connector columns, each connector column comprising a plurality of connector struts, each connector strut connected between two adjacent serpentine bands.

7. The stent of claim 6, wherein the connector columns comprise alternating first connector columns and second connector columns, the first connector columns having connector struts that are different from the connector struts of the second connector columns.

8. The stent of claim 1, wherein the stent is self-expanding and an expanded configuration of the second region comprises a greater diameter than an expanded configuration of the first region.

9. The stent of claim 1, wherein the first serpentine band and the second serpentine band are connected to one another by a plurality of connectors, each connector connects one first strut of the first serpentine band to one turn of the second serpentine band.

10. A stent having a proximal end and a distal end, the stent comprising:
    a tubular body, the tubular body comprising a proximal end region, a central region and a distal end region, each region of the tubular body defined by a plurality of serpentine bands, each serpentine band comprising a plurality of alternating proximal turns and distal turns connected by struts;
    the central region comprising a first serpentine band and a second serpentine band that overlap one another about a common stent circumference, all proximal turns of the first serpentine band aligned about a common stent circumference, all distal turns of the first serpentine band aligned about a common stent circumference, the second serpentine band and the first serpentine band having the same shape;
    the proximal end region and the distal end region each comprising a serpentine band that is not overlapped by another serpentine band; and
    an appendage, the appendage comprising a free end located in the central region, wherein the free end and the struts of a serpentine band of the central region overlap one another about a common stent circumference.

11. The stent of claim 10, the appendage connected at a connected end to a serpentine band in the proximal end region.

12. The stent of claim 11, wherein the appendage does not connect to stent structure located in the central region.

13. The stent of claim 11, wherein the connected end connects to a proximal peak of the serpentine band and extends in a distal direction.

14. The stent of claim 11, wherein the connected end connects to a strut of the serpentine band.

15. The stent of claim 10, further comprising a plurality of appendages.

16. The stent of claim 15, further comprising a plurality of linking members, each linking member connected between two adjacent appendages.

17. The stent of claim 16, wherein the appendages and linking members comprise a serpentine waveform.

18. The stent of claim 10, the free end of the appendage comprising a peak.

19. The stent of claim 18, wherein the appendage is connected at one end to a serpentine band in the proximal end region, extends into the central region, loops back at said peak and extends back into the proximal end region.

20. A stent having a proximal end and a distal end, the stent comprising:
> a tubular body, the tubular body comprising a first region and a second region, each region of the tubular body defined by a plurality of serpentine bands, each serpentine band comprising a plurality of alternating proximal turns and distal turns connected by struts, at least one serpentine band of the first region shaped differently from a serpentine band of the second region;
>
> the second region comprising a first serpentine band and a second serpentine band that overlap one another about a common stent circumference, all proximal turns of the first serpentine band aligned about a common stent circumference, all distal turns of the first serpentine band aligned about a common stent circumference, each serpentine band of the second region having the same shape, the first serpentine band and the second serpentine band connected to one another by a plurality of connectors, each connector attached to a strut of the first serpentine band and a turn of the second serpentine band; and
>
> each serpentine band located in the first region of the stent occupying a separate and distinct length portion of the stent.

* * * * *